United States Patent
Ortega

(10) Patent No.: US 10,022,398 B2
(45) Date of Patent: Jul. 17, 2018

(54) SUPPLEMENTED ANTACID FORMULATION

(71) Applicant: Victor Ortega, Miami, FL (US)

(72) Inventor: Victor Ortega, Miami, FL (US)

( * ) Notice: Subject to any disclaimer, the term of this patent is extended or adjusted under 35 U.S.C. 154(b) by 110 days.

(21) Appl. No.: 14/620,986

(22) Filed: Feb. 12, 2015

(65) Prior Publication Data

US 2017/0136061 A1    May 18, 2017

Related U.S. Application Data

(60) Provisional application No. 62/086,283, filed on Dec. 2, 2014.

(51) Int. Cl.

| | |
|---|---|
| *A61K 33/00* | (2006.01) |
| *A61K 33/10* | (2006.01) |
| *A61K 38/43* | (2006.01) |
| *A61K 36/484* | (2006.01) |
| *A61K 36/906* | (2006.01) |
| *A61K 31/198* | (2006.01) |
| *A61K 31/015* | (2006.01) |
| *A61K 45/06* | (2006.01) |
| *A61K 31/555* | (2006.01) |
| *A61K 36/886* | (2006.01) |
| *A61K 36/73* | (2006.01) |
| *A61K 36/235* | (2006.01) |
| *A61K 36/28* | (2006.01) |
| *A61K 36/54* | (2006.01) |
| *A61K 31/352* | (2006.01) |
| *A61K 38/39* | (2006.01) |
| *A61K 31/05* | (2006.01) |
| *A61K 35/745* | (2015.01) |
| *A61K 35/747* | (2015.01) |

(52) U.S. Cl.
CPC ............ *A61K 33/10* (2013.01); *A61K 31/015* (2013.01); *A61K 31/05* (2013.01); *A61K 31/198* (2013.01); *A61K 31/352* (2013.01); *A61K 31/555* (2013.01); *A61K 33/00* (2013.01); *A61K 35/745* (2013.01); *A61K 35/747* (2013.01); *A61K 36/235* (2013.01); *A61K 36/28* (2013.01); *A61K 36/484* (2013.01); *A61K 36/54* (2013.01); *A61K 36/73* (2013.01); *A61K 36/886* (2013.01); *A61K 36/906* (2013.01); *A61K 38/39* (2013.01); *A61K 38/43* (2013.01); *A61K 45/06* (2013.01)

(58) Field of Classification Search
None
See application file for complete search history.

(56) References Cited

U.S. PATENT DOCUMENTS 8,574,639 B2 * 11/2013 Konn .................... A61K 36/258
424/725

OTHER PUBLICATIONS

Niiko et al., Japan. J. Pharmacol. 21, 177 (1977).*
Javacid—https://www.javacid.com/t-faq.aspx, accessed Apr. 18, 2017.*
Turpie et al., Gut, Apr. 1, 1969 (Apr. 1, 1969), pp. 299-302.*
Jillee—http://www.onegoodthingbyjillee.com/2013/03/24-natural-home-remedies-for-heartburn.html, accessed Apr. 21, 2017.*

* cited by examiner

*Primary Examiner* — Irene Marx
(74) *Attorney, Agent, or Firm* — Malloy & Malloy, P.L.

(57) ABSTRACT

A supplemented antacid formulation comprising at least one primary component and at least one supplemental component. In one embodiment, a primary component is selected from the group consisting of calcium carbonate, magnesium carbonate, and potassium bicarbonate, and a supplemental component is selected from the group consisting of L-glutamine, deglycyrrhizinated licorice, D-limonene, papain, ginger extract, zinc L-carnosine complex, and a probiotic blend. In one further embodiment, a supplemented antacid formulation comprises a plurality of primary components in combination with a plurality of supplemental components, wherein the primary components are selected from the group consisting of calcium carbonate, magnesium carbonate, and potassium bicarbonate, and the supplemental components are selected from the group consisting of L-glutamine, deglycyrrhizinated licorice, D-limonene, papain, ginger extract, zinc L-carnosine complex, and a probiotic blend.

2 Claims, No Drawings

SUPPLEMENTED ANTACID FORMULATION

CLAIM OF PRIORITY

The present application is based on and a claim of priority is made under 35 U.S.C. Section 119(e) to a provisional patent application that is in the U.S. Patent and Trademark Office, namely, that having Ser. No. 62/086,283 and a filing date of Dec. 2, 2014, and which is incorporated herein by reference.

BACKGROUND OF THE INVENTION

Field of the Invention

The present invention is directed to a supplemented antacid formulation having at least one primary component for relief of the symptoms of acid reflux and/or other gastro-intestinal maladies, such as heartburn, in combination with one or more supplemental component for the prevention of acid reflux and/or other gastro-intestinal maladies.

Description of the Related Art

Antacids are commonly administered to persons suffering from occasional heartburn, acid reflux, and/or other common gastro intestinal aliments. Typically, antacids are selected for their basic properties, and often include salts of one or more alkaline anions. Antacids preferably provide nearly instantaneous relief to persons suffering the symptoms of heartburn, however, they often fail to address the causes of heartburn, and as such, it is not uncommon for antacids to be taken in excess by persons who suffer from heartburn, acid reflux, and/or other such gastro intestinal aliments.

For persons suffering from regularly occurring or chronic heartburn, acid reflux, and/or other common gastro intestinal aliments, a variety of compounds and/or formulations have been administered to reduce the frequency and/or severity of the symptoms experienced by a user. Many of these compounds and/or formulations are provided by prescription only, and as a result, they are not as readily available as over-the-counter products due to cost and/or convenience to obtain by end users. Furthermore, unlike antacids, these preventative compounds and/or formulations typically do not provide immediate relief from the symptoms of heartburn. As such, it is not uncommon for persons using a compound and/or formulation for regularly occurring or chronic heartburn to also take one or more antacids for immediate relief. However, antacids may be contraindicated when a person is already using a compound and/or formulation to reduce the frequency and/or severity of the symptoms experienced by a user.

As such, it would be beneficial to provide an antacid formulation including one or supplemental compounds which are not contraindicated for use in combination with the same. It would further be beneficial to provide an antacid formulation including one or supplemental compounds which not only are not contraindicated, but also help minimize instances of chronic heartburn, acid reflux, and/or other common gastro intestinal aliments when regularly administered to a user. A further benefit may be realized by providing an antacid formulation including one or supplemental compounds comprised solely of over-the-counter components so as to improve accessibility to all persons who suffer from acid reflux and/or other gastro-intestinal maladies.

SUMMARY OF THE INVENTION

The present invention, in one embodiment, is directed to a supplemented antacid formulation comprising at least one primary component selected from the group consisting of calcium carbonate, magnesium carbonate, and potassium bicarbonate, and at least one supplemental component selected from the group consisting of deglycyrrhizinated licorice, ginger extract, glutamine, D-limonene, papaya enzymes, a prebiotic blend, a probiotic blend, zinc L-carnosine complex, aloe vera, apple cider vinegar, fennel seeds, chamomile, cinnamon, quercetin, collagen, and resveratrol.

A further embodiment of the present invention is directed to a supplemented antacid formulation comprising a plurality of primary components selected from the group consisting of calcium carbonate, magnesium carbonate, and potassium bicarbonate, and a plurality of supplemental components selected from the group consisting of deglycyrrhizinated licorice, ginger extract, glutamine, D-limonene, papaya enzymes, a prebiotic blend, a probiotic blend, zinc L-carnosine complex, aloe vera, apple cider vinegar, fennel seeds, chamomile, cinnamon, quercetin, collagen, and resveratrol.

A unit dosage of a supplemented antacid formulation in accordance with at least one embodiment of the present invention comprises at least one primary component in an amount of about 50 to 2,000 milligrams. In at least one further embodiment, a unit dosage of a supplemented antacid formulation comprises at least one primary component in an amount of about 100 to 1,000 milligrams. Further, a unit dosage of a supplemented antacid formulation in accordance with at least one other embodiment comprises at least one supplemental component in an amount of about 10 to 2,000 milligrams, and in one further embodiment, a supplemented antacid formulation comprises at least one supplemental component in an amount of about 10 to 1,000 milligrams.

These and other objects, features and advantages of the present invention will become clearer when the detailed description is taken into consideration.

DETAILED DESCRIPTION

As noted above, the present invention is directed to a supplemented antacid formulation having at least one primary component for relief of the symptoms of acid reflux and/or other gastro-intestinal maladies, in combination with one or more supplemental component for the prevention of acid reflux and/or other gastro-intestinal maladies.

In one embodiment, a primary component is selected from components generally exhibiting basic or acid-neutralizing properties which may be safely ingested in effective amounts by a person for relief of the symptoms of acid reflux and/or other gastro-intestinal maladies. A primary component may comprise an alkaline ion to directly neutralize gastric acids in a person's stomach. In one further embodiment, a primary component in accordance with the present invention comprises a salt, for example, a chemical salt of an alkaline ion and at least one counterion.

By way of example only, a primary component of a supplemented antacid formulation in accordance with at least one embodiment of the present invention may comprise, but is in no manner limited to, an aluminum carbonate gel (basic), aluminum hydroxide, aluminum hydroxide-hexitol stabilized polymer, aluminum hydroxide-magnesium carbonate co-dried gel, aluminum hydroxide-magnesium tri-silicate co-dried gel, hydrated aluminum hydroxide-sucrose powder, aluminum phosphate, aluminum phosphate gel, bicarbonate, bismuth aluminate, bismuth carbonate, bismuth subcarbonate, bismuth subgailate, bismuth subnitrate, calcium (mono or dibasic salt), calcium carbonate, calcium phosphate, activated charcoal, citrate ion as citric acid or citric salt, dihydroxyaluminum aminoacetate, dihydroxyaluminum aminoacetic acid, dihydroxyaluminum sodium carbonate, glycine (aminoacetic acid), hydrate magnesium aluminate activated sulfate, magaldrate, magnesium aluminosilicate, magnesium carbonate, magnesium glycinate, magnesium hydroxide, magnesium oxide, magnesium trisilicate, dried milk solids, potassium bicarbonate, potassium carbonate, simethicone (poly(dimethyl)siloxane and hydrated silica gel), sodium bicarbonate, sodium carbonate, sodium potassium tartrate, tartrate (acid or salt), or tricalcium phosphate.

At least one embodiment of a supplemented antacid formulation in accordance with the present invention comprises at least one primary component selected from the group consisting of calcium carbonate, magnesium carbonate, and potassium bicarbonate, and another embodiment comprises a plurality of primary components selected from the group consisting of calcium carbonate, magnesium carbonate, and potassium bicarbonate. A further embodiment of a supplemented antacid formulation in accordance with the present invention comprises a plurality of primary components, wherein the plurality of primary components include calcium carbonate, magnesium carbonate, and potassium bicarbonate.

A unit dosage of a supplemented antacid formulation in accordance with at least one embodiment of the present invention comprises at least one primary component in an amount of about 50 to 2,000 milligrams. In at least one further embodiment, a unit dosage of a supplemented antacid formulation comprises at least one primary component in an amount of about 100 to 1,000 milligrams, and in another embodiment, a unit dosage of a supplemented antacid formulation in accordance with the present invention comprises at least one primary component in an amount of about 500 milligrams. Yet one further embodiment of a supplemented antacid formulation in accordance with the present invention comprises a plurality of primary components in an amount of about 500 milligrams each.

As also noted above, a supplemented antacid formulation in accordance with the present invention includes one or more supplemental components for the prevention of acid reflux and/or other gastro-intestinal maladies. In at least one embodiment, a supplemental component serves to protect the lining of the gastrointestinal tract, or the mucosa, such as glutamine. A supplemental component may demonstrate an inhibitory effect on the growth of *H. pylori*, a bacterium linked to the development of duodenal ulcers and stomach cancer, such as certain zinc-carnosine complexes. In yet one further embodiment, a supplemental component relieves the symptoms of chronic heartburn, gastroesophageal reflux disease (GERD), gastro-oesophageal reflux disease (GORD), gastric reflux disease, and/or acid reflux disease, such as D-limonene.

A supplement component in one embodiment of a supplemented antacid formulation in accordance with at least one embodiment of the present invention comprises a prebiotic/probiotic blend of helpful bacterium which improve intestinal function and maintain the sensitive lining of the intestine, thereby eliminating potential sources for acid reflux and/or other gastro-intestinal maladies.

In at least one embodiment of a supplemented antacid formulation in accordance with the present invention, a supplemental component may also serve to aid in the digestive processes and functioning of the intestines, such as papaya enzymes and ginger extracts, once again, eliminating a potential source of heartburn and/or other gastro-intestinal maladies. In yet one further embodiment, a supplemental component serves to stimulate secretion of mucous in the stomach, thereby helping prevent ulcer formation and providing relief from heartburn and other gastric maladies, such as deglycyrrhizinated licorice or DGL.

Once again, by way of example only, a supplemental component of a supplemented antacid formulation in accordance with at least one embodiment of the present invention may comprise, but is in no manner limited to, deglycyrrhizinated licorice, ginger extract, glutamine, D-limonene, papaya enzymes, a prebiotic blend, a probiotic blend, zinc L-carnosine complex, aloe vera, apple cider vinegar, fennel seeds, chamomile, cinnamon, quercetin, collagen, and resveratrol.

At least one embodiment of a supplemented antacid formulation in accordance with the present invention comprises at least one supplemental component selected from the group consisting of deglycyrrhizinated licorice, ginger extract, glutamine, D-limonene, papaya enzymes, a probiotic blend, and a zinc L-carnosine complex. One other embodiment comprises plurality of supplemental components selected from the group consisting of deglycyrrhizinated licorice, ginger extract, glutamine, D-limonene, papaya enzymes, a probiotic blend, and a zinc L-carnosine complex. At least one further embodiment of a supplemented antacid formulation in accordance with the present invention comprises a plurality of supplemental components including deglycyrrhizinated licorice, ginger extract, glutamine, D-limonene, papaya enzymes, a probiotic blend, and a zinc L-carnosine complex.

A unit dosage of a supplemented antacid formulation in accordance with at least one embodiment of the present invention comprises at least one supplemental component in a supplementary amount of about 10 to 2,000 milligrams. In at least one further embodiment, a unit dosage of a supplemented antacid formation comprises at least one supplemental component in an amount of about 10 to 1,000 milligrams.

In yet one further embodiment of a supplemented antacid formulation in accordance with the present invention, a unit dosage comprises supplemental amounts of a plurality of supplemental components including about 1,000 milligrams of L-glutamine, about 500 milligrams of deglycyrrhizinated licorice, about 500 milligrams of D-limonene, about 500 milligrams of papain, wherein said papain comprises about 2,000 U.S.P. units per milligram, about 120 milligrams of said ginger extract, about 35 to 40 milligrams of zinc L-carnosine complex, and about 10 to 15 milligrams of a probiotic blend, wherein said probiotic blend comprises a mixture of *B. Bifidum, B. Longum, L. Acidophilus, L. Rhamnosous*, and *L. Casei* and comprises 200 billion colony forming units per gram.

In addition to the aforementioned primary components and supplemental components, in at least one embodiment, a supplemented antacid formulation in accordance with the present invention further comprises one or more ancillary components. As one example, an ancillary component comprises an amount of a sugar substitute including steviol glycosides, for example, stevioside and rebaudioside, such as is sold under the brand name STEVIA®. Another embodiment comprises an amount of silicon dioxide as an ancillary component. In yet one further embodiment, an ancillary component comprises an amount of citric acid, sodium chloride, and/or natural orange flavor.

In at least one embodiment, a unit dosage of a supplemented antacid formulation in accordance with the present invention comprises about 90 to 95 milligrams of STEVIA® (98%), about 70 to 75 milligrams of silicon dioxide, about 1,450 to 1,500 milligrams of citric acid, about 80 milligrams of natural orange flavor, and about 5 to 10 milligrams of sodium chloride.

Although various compositions of a unit dosage of a supplemented antacid formulation in accordance with the present invention are disclosed herein, there is no prescribed dosage regimen for the present formulation. That is to say, the present supplemented antacid formulation is intended to be taken by a user on an as needed basis.

In at least one embodiment, the primary components and supplemental components of a supplemented antacid formulation in accordance with the present invention are admixed together to form a homogenous powder which is readily dissolved in water or another aqueous based solvent prior to administration to a user. In yet one further embodiment, the primary components and supplemental components of a supplemented antacid formulation in accordance with the present invention are admixed together and formed into tablets or placed into capsules for ease of distribution and administration to a user. In yet another embodiment, the primary components and the supplementary components of a supplemented antacid formulation are mixed together to form a homogenous liquid solution which may be ingested directly, or may be placed into liquid gel caps.

In one preferred embodiment, the primary components and supplemental components of a supplemented antacid formulation in accordance with the present invention exhibit effervescence properties when dissolved in water or another aqueous based solvent prior to administration to a user. Stated otherwise, in at least one embodiment, a supplemented antacid formulation in accordance with the present invention is effervescent, and may be formed into tablets or remain as a dry powder prior to dissolution into water or other aqueous solvent which a user may drink as needed.

Since many modifications, variations and changes in detail can be made to the described preferred embodiment of the invention, it is intended that all matters in the foregoing description be interpreted as illustrative and not in a limiting sense. Thus, the scope of the invention should be determined by the appended claims and their legal equivalents.

Now that the invention has been described,

What is claimed is:
1. A supplemented antacid formulation comprising:
a plurality of primary components for relief of the symptoms of acid reflux including calcium carbonate in an amount of about 500 milligrams, magnesium carbonate in an amount of about 500 milligrams, and potassium bicarbonate in an amount of about 500 milligrams, and
a plurality of supplemental components including deglycyrrhizinated licorice in an amount of about 500 milligrams, ginger in an amount of about 120 milligrams, glutamine in an amount of about 1,000 milligrams, D-limonene in an amount of about 500 milligrams, papaya enzymes in an amount of about 500 milligrams, a probiotic blend in an amount of about milligrams to about 15 milligrams, wherein said probiotic blend comprises a mixture of *B. Bifidum, B. Longum, L. Acidophilus, L. Rhamnosous*, and *L. Casei* comprising $2\times10^{11}$ colony forming units per gram (CFU/g), and zinc L-carnosine in an amount of about 35 milligrams to about 40 milligrams.
2. The formulation as recited in claim further comprising one or more components including a prebiotic blend, aloe vera, apple cider vinegar, fennel seeds, chamomile, cinnamon, quercetin, collagen, and/or resveratrol.

* * * * *